United States Patent [19]

Suzuki et al.

[11] Patent Number: 5,027,688

[45] **Date of Patent: * Jul. 2, 1991**

[54] BRACE TYPE ANGLE-DETECTING DEVICE FOR MUSICAL TONE CONTROL

[75] Inventors: Hideo Suzuki; Shunichi Matsushima; Masahiko Obata; Masao Sakama, all of Hamamatsu, Japan

[73] Assignee: Yamaha Corporation, Hamamatsu, Japan

[*] Notice: The portion of the term of this patent subsequent to Mar. 6, 2007 has been disclaimed.

[21] Appl. No.: 352,104

[22] Filed: May 15, 1989

[30] Foreign Application Priority Data

May 18, 1988 [JP] Japan .............................. 63-121493
May 18, 1988 [JP] Japan .............................. 63-121494

[51] Int. Cl.5 ........................ G10H 1/18; G10H 1/32; A61B 5/11

[52] U.S. Cl. .................................... 84/600; 128/782; 73/865.4

[58] Field of Search ................ 84/600, 615, 653, 678, 84/742, 453, 723; 128/782; 33/1 PT, DIG. 13; 73/865.4

[56] References Cited

U.S. PATENT DOCUMENTS 1,041,252 10/1912 Dougherty .................... 128/782 X
1,590,499 6/1926 Cozad ................................ 128/782
3,704,339 11/1972 Niinomi .
3,705,948 12/1972 Tomisawa .
4,436,099 3/1984 Raftopoulos ........................ 128/782
4,444,205 4/1984 Jackson .............................. 128/782
4,526,078 7/1985 Chadabe .......................... 84/615 X
4,608,998 9/1986 Murdock ............................ 128/782
4,627,324 12/1986 Zwosta ........................ 84/477 R X
4,665,928 5/1987 Linial et al. ........................ 128/781
4,667,685 5/1987 Fine .................................... 128/782
4,745,930 5/1988 Confer .......................... 128/782 X
4,804,001 2/1989 McLeod, Jr. ...................... 128/782

FOREIGN PATENT DOCUMENTS 0264782 10/1987 European Pat. Off. .
63-96697 4/1988 Japan .

*Primary Examiner*—W. B. Perkey
*Attorney, Agent, or Firm*—Spensley Horn Jubas & Lubitz

[57] ABSTRACT

A brace type angle-detecting device for musical tone control includes a brace to be fit around a joint portion of a player and an angle-detecting mechanism mounted on the brace for detecting the bending angle of the player's joint and producing a musical tone control signal in response to the angle of the player's joint. The angle-detecting mechanism includes first and second elongated members detachably mounted on the brace which are connected to one another so as to be pivotable in a bending direction of the player's joint. The device includes a fastener for tightly fastening the brace to a body member of the player.

4 Claims, 5 Drawing Sheets

BRACE TYPE ANGLE-DETECTING DEVICE FOR MUSICAL TONE CONTROL

BACKGROUND OF THE INVENTION

This invention relates to a brace type detecting device for musical tone control for controlling a musical tone in response to movement at several articulations of the player. More specifically, this invention relates to a brace type detecting device for a musical tone control system such as shown in U.S. patent application Ser. No. 281,553.

Conventionally, a musical tone is generated by playing a musical instrument such as a piano, a violin or the like or by use of the vocal chords of the player. Proven musical instruments cannot convert a body action of a player such a rhythmic exercise into a musical tone.

SUMMARY OF THE INVENTION

It is therefore an object of the present invention to provide a brace type angle-detecting device for musical control.

According to one aspect of the present invention, there is provided a brace type angle-detecting device for musical tone control. The brace type angle-detecting device includes a brace to be fit around articulations of the player; and an angle-detecting mechanism mounted on the brace for detecting the bending angle of the player's joint and producing a musical tone control signal in response to the angle of the player's joint. The musical tone control signal is transmitted to a musical tone control data-generating circuit for generating musical tone control data, thereby controlling the musical tone. Therefore, a body action such as a rhythmic exercise can effect control parameters of the musical tone.

The angle-detecting mechanism is removably attached to the brace. Therefore, when the brace is stained by e.g., sweat, it can be washed. If the angle-detecting mechanism malfunctions, it may be easily replaced by a new one.

It is desirable that the angle-detecting device for musical tone control includes a fastener for tightly fastening the brace to the player's joint portion.

DETAILED DESCRIPTION OF THE PREFERRED EMBODIMENTS

The present invention will now be described with reference to the accompanying drawings.

Figure 5:
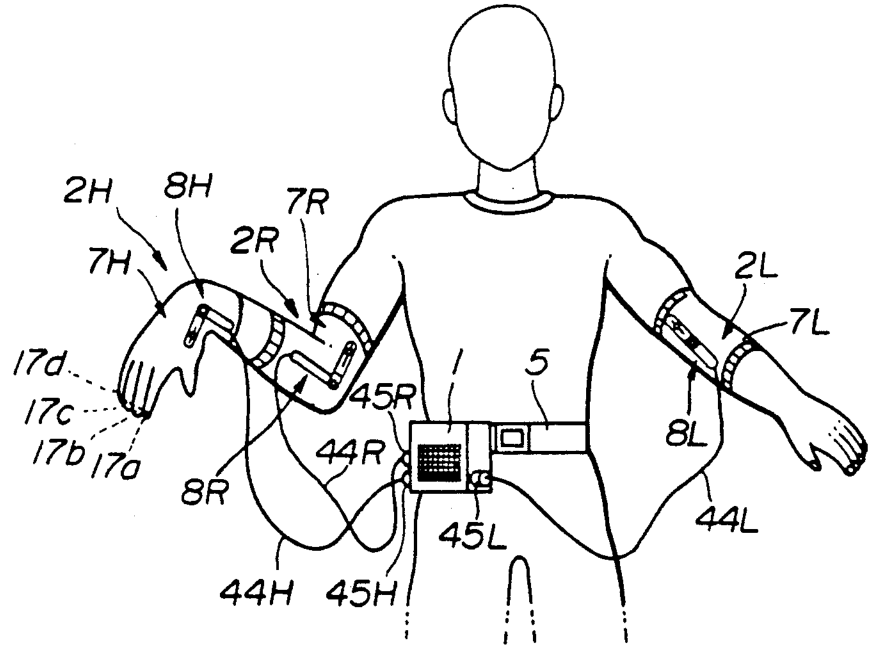
FIG. 5 is a front view showing the overall configuration of a musical tone control system which uses the brace type detecting device shown in FIG. 1.
Figure 6:
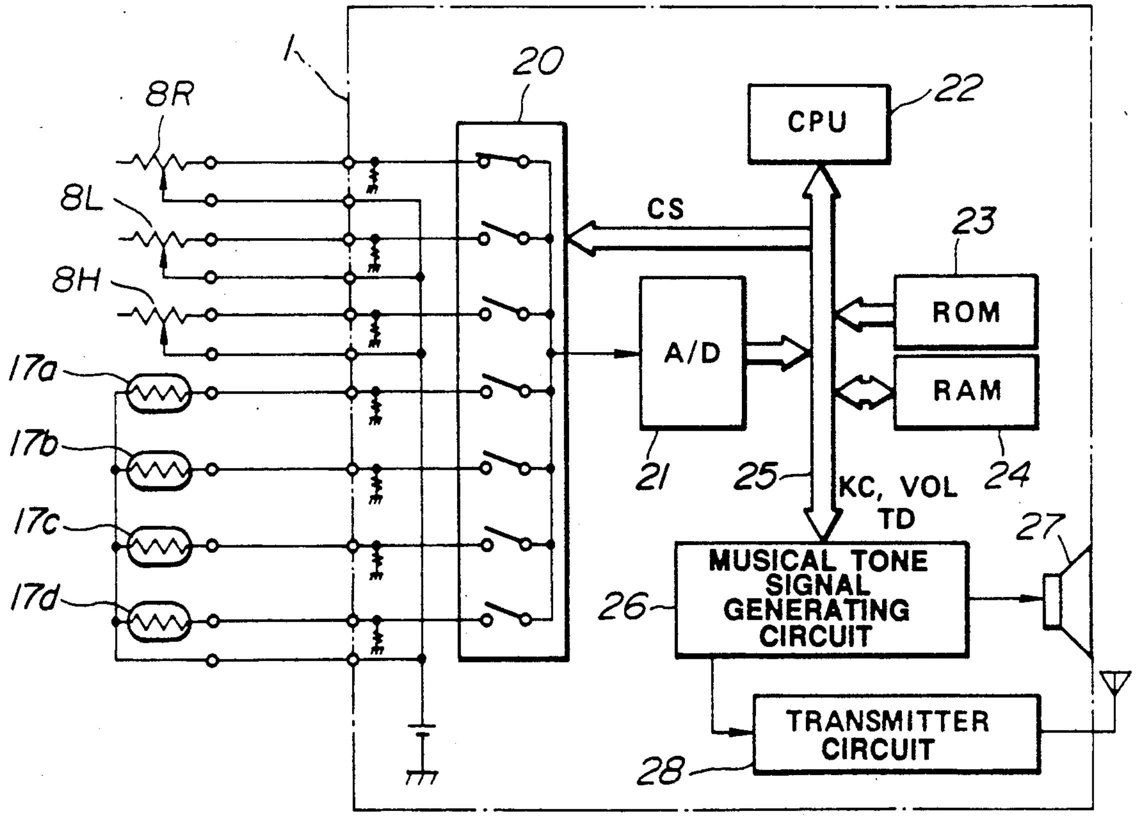
FIG. 6 is a block diagram showing the electrical configuration of the musical tone control system shown in FIG. 5.

FIG. 5 shows the configuration of the musical tone control system. This musical tone control system consist of main circuit 1, brace type detecting device 2R for detecting motion of the player's right elbow, brace type detecting device 2L for detecting motion of the player's left elbow, and glove type detecting device 2H for detecting motion of the player's right hand. Main circuit 1 is fitted to the player's waist by belt 5 and detecting devices 2R, 2L, and 2H are mounted on the player's right elbow, left elbow, and right hand, respectively. Main circuit 1 comprises not only a musical tone control apparatus but also musical tone signal generating circuit 26 controlled by the musical tone control device, and speaker 27 as shown in FIG. 6.

Figure 1:
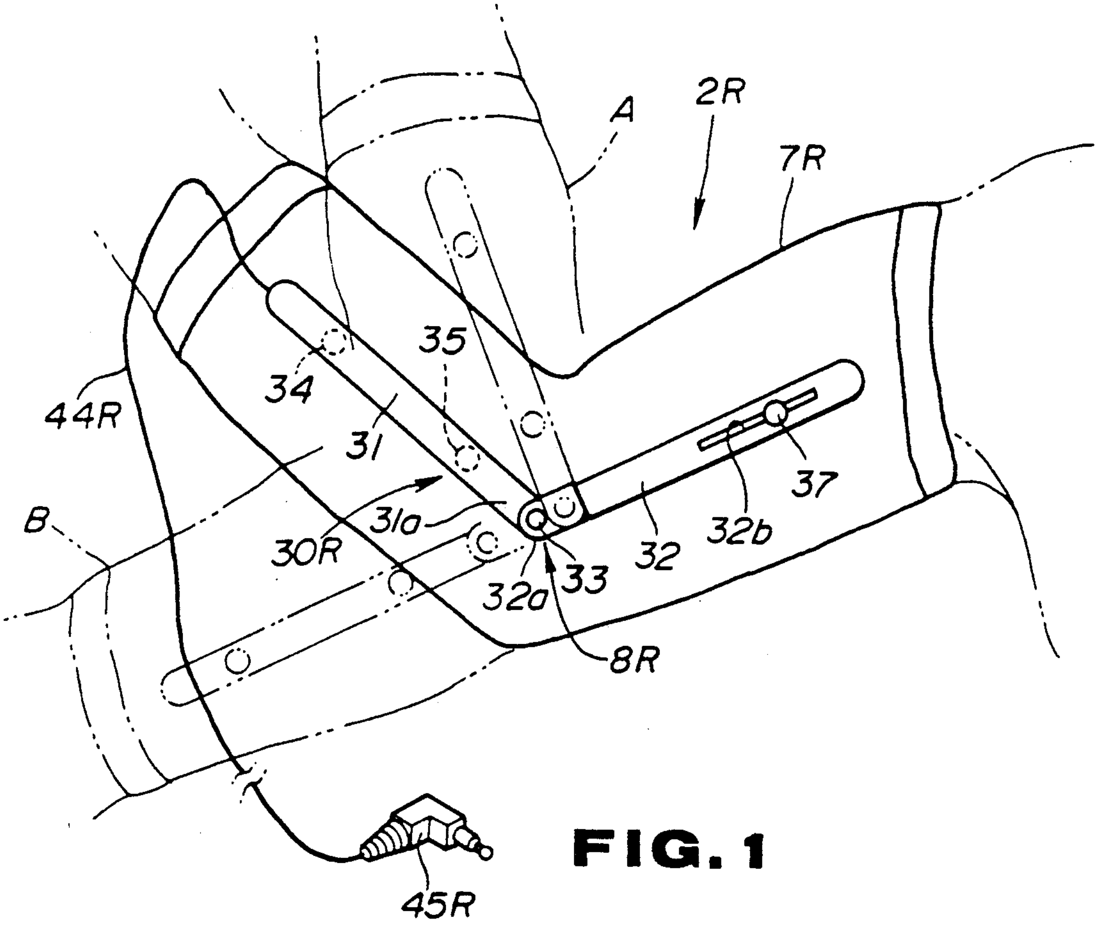
FIG. 1 is a front elevation showing the configuration of a brace type detecting device for a player's right elbow according to a first preferred embodiment of the present invention.

Brace type detecting device 2R, as shown in FIG. 1, includes brace 7R fit on the elbow of the player's right arm and angle detector 8R. Brace 7R consists of an elastic material such as ENEL 8000 trademark) composed of 84% of nylon and 16% of polyurethane.

Figure 2:
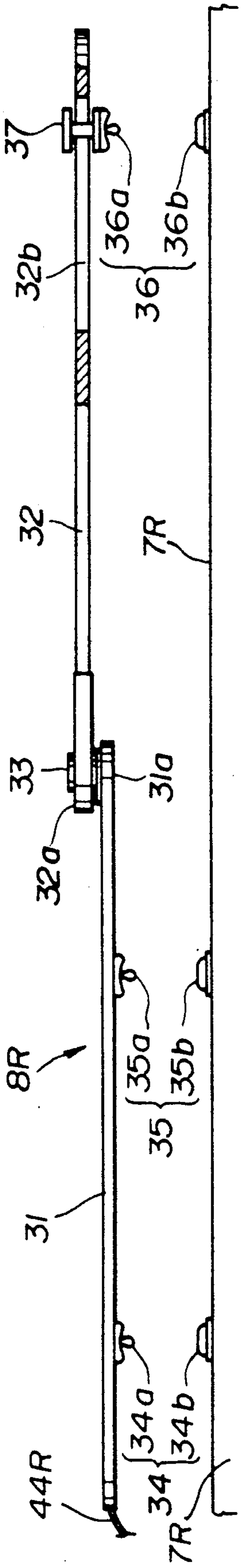
FIGS. 2 and 3 are, respectively, a partial broken side elevation and a front elevation showing an angle-detector used in the detecting device shown in FIG. 1.
Figure 3:
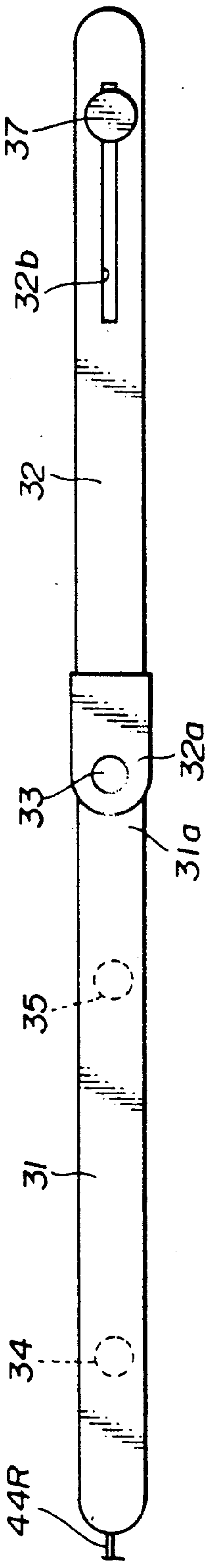

Angle detector 8R has first and second elongated elements 31 and 32 rotatably connected to each other at each's respective end 31*a* and 32*a* by pin 33. Elongated elements 31 and 32 consist of elongated plastic plates or the like of about the same size and removably mounted on brace 7R with snaps 34, 35, and 36 as shown in FIGS. 1, 2, and 3. First elongated element 31 is removably mounted on brace 7R with snaps 34 and 35. Male snaps 34*a* and 35*a* of snaps 34 and 35 are attached to the back of the elongated element 31, whereas the female snaps 34*b* and 35*b* to which male snaps 34*a* and 35*a* are to be fixed are attached to the brace 7R. On the other hand, second elongated element 32 is provided with lengthwise slot 32*b* into which guide member 37 is slidably fitted. Male snap 36*a* of snap 36 is attached to the back of guide member 37, and female snap 36*b* to which male snap 36*a* is to be fixed is attached to brace 7R.

Figure 4:
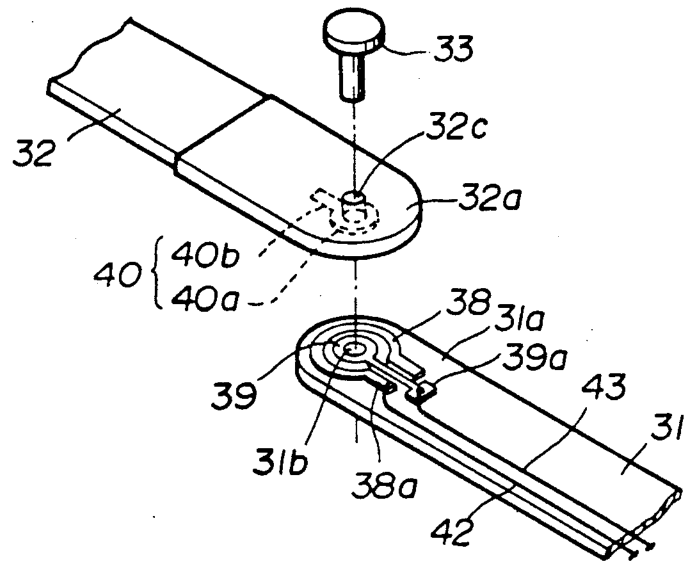
FIG. 4 is an exploded perspective view showing the main portion of the angle detector shown in FIGS. 1, 2, and 3.

At the jointing ends of elongated elements 31 and 32, as shown in FIG. 4, there are provided resistance element 38, fixed contact 39, and sliding contact 40 functioning as a potentiometer. More specifically, elongated element 31 is provided with hole 31*b* for inserting and fixing pin 33; around hole 31*b* there is provided fixed contact 39. Semicircular resistance element 38 is formed surrounding fixed contact 39 with hole 31*b* as its center point. On the other hand, at the end of elongated element 32, there is provided hole 32*c* into which pin 33 is inserted loosely; around hole 32*c*, there is provided sliding contact 40. Sliding contact 40 comprises ring portion 40*a* which maintains contact with fixed contact 39, and projection 40*b* which slides on resistance element 38 maintaining contact therewith. Lead wire 42 is connected to terminal 38*a* at the end of the resistance element 38 and lead wire 43 is connected to terminal 39*a* at the end of fixed contact 39. Lead wires 42 and 43 are joined with connector 45R via cable 44R as shown in FIG. 1.

Brace type detecting device 2R whose construction is described above is mounted on the player's right arm as shown in FIG. 1. More specifically, on the portion of the upper arm covered by brace 7R, second elongated element 32 is mounted by guide member 37 attached to brace 7R by snap 36 (at one point) so that elongated element 32 is able to slide longitudinally. On the other hand, on the portion of the forearm covered by brace 7R, elongated element 31 is attached by snaps 34 and 35 (at two points). When the player's right arm bends as shown by broken line A in FIG. 1, or stretches it as shown by broken line B, elongated element 31 rotates about pin 33. Accompanying the rotation, projection 40*b* of sliding contact 40 slides on resistance element 38. As a result, resistance between terminal 38*a* of resistance element 38*a* and terminal 39*a* of fixed contact 39 varies in response to the displacement of sliding contact 40, that is, the bending angle of the right arm. In this case, motion of the player's arm is unrestricted because guide member 37 slides along slots 32*b* in response to rotation of elongated element 32 with flexing or extending of the arm.

Brace type detecting device 2L for the left elbow, as shown in FIG. 5, consists of brace 7L to be fit on the player's left elbow joint portion and an angle detector 8L removable mounted on brace 7L. In addition, detecting device 2H for the right hand consists of a glove 7H and an angle detector 8H removably mounted on glove 7H. Glove 7H is provided with strain transducers 17*a*–17*d* at the palmer aspect of the four finger tips. Since angle detectors 8L and 8H are similar to the above mentioned angle detector 8R, description thereof will be omitted.

The signal outputted from angle detector 8R of detecting device 2R for the player's right elbow is first led to cable 44R, and then conveyed to main circuit 1. Similarly, the signals outputted from angle detector 8L and 8H of detecting device 2L and 2H for the player's left elbow and right hand are first led to cable 44L and 44H, respectively, and then conveyed to the main circuit 1.

The construction of main circuit is shown in FIG. 6. In FIG. 6, 20 denotes a seven-channel analog multiplexer which can select one of the detection signals (voltage signals) delivered from angle detectors 8R, 8L, and 8H and strain transducers 17*a*–17*d* based on the channel-selection signal CS applied to a selection terminal thereof. A/D converter (analog-to-digital converter) 21 converts a detection signal from analog multiplexer 20 into digital detection data of predetermined bit pattern. CPU (central processing unit) 22 controls the musical tone control system using programs stored in ROM (read only memory) 23. RAM (random access memory) 24 is used as a work area. CPU 22 supplies the sequentially varying channel-selection signal CS to the analog multiplexer 20 so that the outputs of angle detectors 8R, 8L, and 8H and strain transducers 17*a*–17*d* are scanned at a high speed. In addition, CPU 22 determines the bending angles of the player's right and left elbows by use of four angle steps based on the detection data from A/D converter 21. On the basis of the angle determination result, CPU 22 generates key code data KC indicating one of the predetermined tone pitches in response to the combination of the bending angles of the player's right and left elbows. Further, CPU 22 determines the bending angle of the right wrist by use of three angle stages based on the detection data which are obtained by converting the signal from angle detector 8H with A/D converter 21. On the basis of the angle determination result, CPU 22 generates tone volume data VOL by selectively designating one of the predetermined three tone volumes (i.e., loud, intermediate, and soft tone volumes) in response to the bending angle of the player's right wrist. Moreover, CPU 22 determines whether any of the four fingers (i.e., index finger, middle finger, ring finger, and little finger) are flexed or not. On the basis of the determination result, CPU 22 generates tone color (timbre) data TD selectively designating one of the predetermined tone colors (timbres such as a piano, an organ, a flute, a saxophone, a clarinet, and the like) in response to the combination of bent fingers. The key code data KC, the tone volume data VOL, and the tone color data TD which are generated in CPU 22 (these date are generically called musical tone control data) are transferred to a musical tone signal generating circuit 26 through bus line 25. Musical tone signal generating circuit 26 generates a musical tone signal having the tone pitch corresponding to the key code data KC, the tone volume corresponding to the tone volume data VOL, and the tone color corresponding to the tone color data TD. The musical tone signal outputted from the musical tone signal generating circuit 26 is supplied to speaker 27 for producing a musical tone as well to as transmitter circuit 28 for transmitting the musical tone signal by wireless.

According to the above described device, the combination of the bending angles of the player's right and left elbows can change the tone pitch of the musical tone produced by speaker 27 in main circuit 1. Furthermore, the bending angle of the player's right wrist can change the musical tone volume at the three steps. Moreover, the combination of flexed fingers among the player's four fingers can change the tone color of the musical tone. Thus, movements of the player can control the musical tone.

While in the description, brace 7R consists of an elastic material such as ENEL 8000 (trademark) composed of 84% of nylon and 16% of polyurethane, braces 7R and 7L and the glove 7H can be made of film like polymeric rubber; a material like artificial skin, for example, such as BION II (trade mark) with high water resistance, high moisture permeability, and high elasticity. This improves movement of elongated elements 31 and 32 constituting angle detectors 8R.

Figure 7:
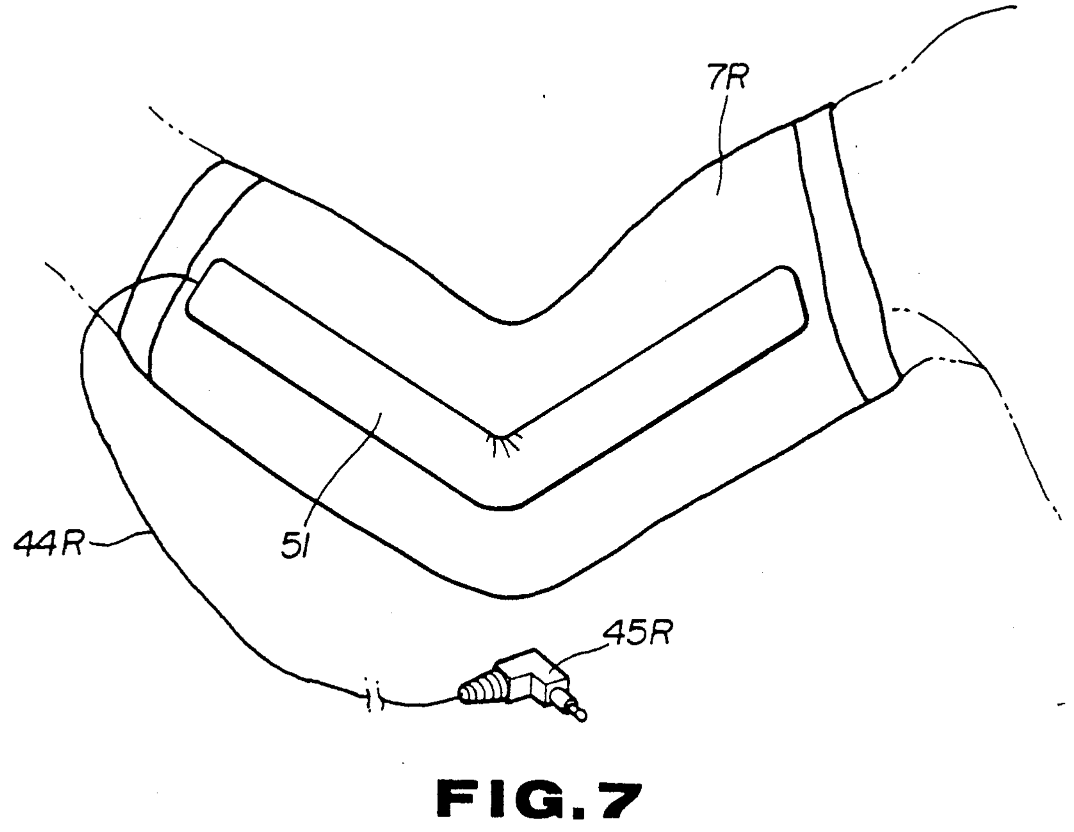
FIG. 7 is a front elevation showing the configuration of brace type detecting device for a player's right elbow according to a second preferred embodiment.

FIG. 7 shows another brace type angle-detecting device for the player's right elbow according to a second preferred embodiment of the present invention. In FIG. 7, brace 7R is made of film like polymeric rubber; such as BION II (trade mark) with high water resistance, high moisture permeability, and high elasticity. This improves movement of elongated elements 31 and 32 constituting angle detector 8R. In addition, angle detector 8R is inserted in flexible waterproof cover 51 and fastened to cover 51, and the cover 51 is attached to brace 7R; the structure thus formed improves resistance to sweat and prevents the player's sweat from accumulating on metal parts such as the resistance element, fixed contact, or the sliding contact.

Figure 8:
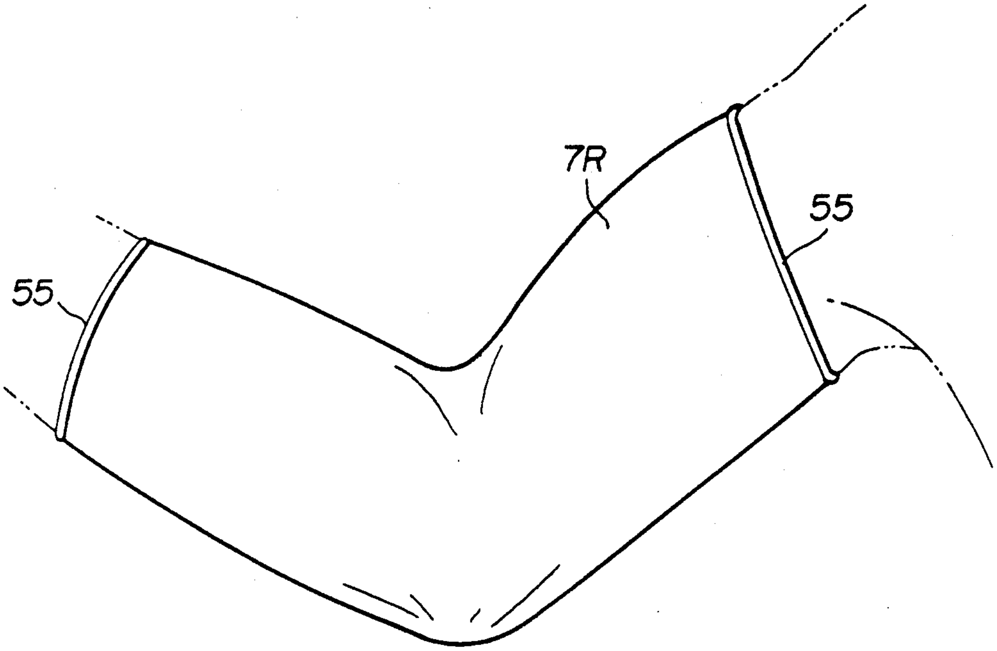
FIG. 8 is a front elevation showing the configuration of brace type detecting device for a player's right elbow according to a third preferred embodiment.

Next, FIG. 8 shows another brace type angle-detecting device for the player's right elbow according to a third preferred embodiment of the present invention. In FIG. 8, brace 7R has two elastic bands 55 at the opposite ends thereof. Elastic bands 55 which may be made of rubber are sewed to brace 7R so as to maintain the position of brace 7R on the player's arm.

Figure 9:
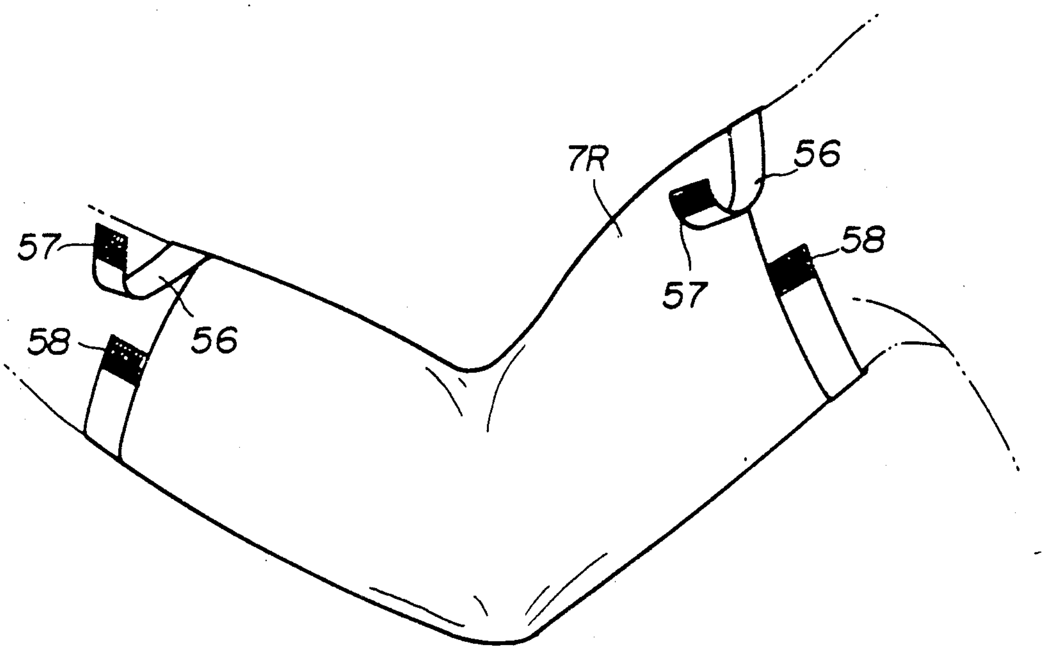
FIG. 9 is a front elevation showing the configuration of brace type detecting device for a player's right elbow according to a fourth preferred embodiment.

FIG. 9 also shows another brace type angle-detecting device for player's right elbow according to a fourth preferred embodiment of the present invention. In FIG. 9, brace 7R has two elastic straps 56 at the opposite ends thereof. Elastic straps 56 are sewed to brace 7R. One end of each elastic strap 56 has hook tape 57 and the other end has loop tape 58, both made of Velcro (trademark), which fasten to each other, so as to maintain the position of brace 7R on the player's arm. In the third and fourth embodiments, because elastic bands 55 or elastic straps 56 maintain the position of brace 7R on the player's arm, brace 7R slippage can be prevented on the player's arm. While it is omitted to show angle detector 8R in the third and fourth embodiments in FIGS. 8 and 9, angular detector 8R is same as the above described type.

What is claimed is:

1. A brace type angle-detecting device for musical tone control, comprising:

a brace to be fit around a joint portion of a player;

tightening means, attached to at least one end of the brace, for tightening the brace to a body member of the player; and angle-detecting means for detecting the bending angle of the player's joint and producing a musical tone control signal in accordance with the angle of the player's joint, thereby controlling a musical tone, the angle-detecting means comprising first and second elongated plates detachably mounted to the brace, one end of the first elongated plate being joined to one end of the second elongated plate such that the first and second elongated plates are pivotable in a bending direction of the player's joint.

2. A brace type angle-detecting device for musical tone control according to claim 1, wherein said tightening means comprises an elastic band.

3. A brace type angle-detecting device for musical tone control according to claim 1, wherein said tightening means comprises an elastic strap which has a loop tape end and a hook tape end each being fastenable to the other.

4. A brace type angle-detecting device for musical tone control, according to claim 1, further comprising a flexible waterproof cover mounted on the brace, said angle-detecting means being inserted in and attached to the cover.

* * * * *